US005958720A

United States Patent [19]

Litwack et al.

[11] Patent Number: 5,958,720

[45] Date of Patent: Sep. 28, 1999

[54] MCH2, AN APOPTOTIC CYSTEINE PROTEASE, AND COMPOSITIONS FOR MAKING AND METHODS OF USING THE SAME

[75] Inventors: Gerald Litwack, Bryn Mawr; Emad S. Alnemri; Teresa Fernandez-Alnemri, both of Ambler, all of Pa.

[73] Assignee: Thomas Jefferson University, Philadelphia, Pa.

[21] Appl. No.: 09/146,331

[22] Filed: Sep. 2, 1998

Related U.S. Application Data

[62] Division of application No. 08/896,885, Jul. 18, 1997, which is a continuation of application No. 08/446,925, May 18, 1995, Pat. No. 5,672,500.

[51] Int. Cl.$^{6}$ .............................. C12Q 1/37; C12N 9/50; C12N 9/64

[52] U.S. Cl. ................................ 435/23; 435/4; 435/219; 435/226

[58] Field of Search ................................. 435/219, 4, 23, 435/226

[56] References Cited

U.S. PATENT DOCUMENTS

| | | | |
|---|---|---|---|
| 4,736,866 | 4/1988 | Leder et al. | 800/2 |
| 4,873,191 | 10/1989 | Wagner et al. | 435/172.3 |
| 5,108,921 | 4/1992 | Low et al. | 435/240.1 |
| 5,672,500 | 9/1997 | Litwack et al. | 435/252.3 |

OTHER PUBLICATIONS

Alnemri et al., "Cloning and Expression of Four Isoforms of Human Interleukin–1β Converting Enzyme with Different Apoptotic Activities," *J. Biol. Chem. 270*: 4312–4317, 1995.

Alnemri et al., "Characterization and Purification of a Functional Rat Glucocorticoid Receptor Overexpression in a Baculovirus System," *J. Biol. Chem. 266*(6): 3925–3936, 1991.

Arad et al., "Use of Reconstituted Sendai Virus Envelopes for Fusion–mediated Microinjection of Double–stranded RNA: Inhibition of Protein Synthesis in Interferon–treated Cells," *Riochimica et Biophysica Acta 859*: 88–94, 1986.

Capecchi, "Altering the Genome by Homologous Recombination," *Science 244*: 1288–1292, 1989.

Casciola–Rosen et al., "Specific Cleavage of the 70–kDa Protein Component of the U1 Small Nuclear Ribonucleoprotein is a Characteristic Biochemical Feature of Apoptotic Cell Death," *J. Biol. Chem. 269*: 30757–30760, 1994.

Cerretti et al., "Molecular cloning of the Interleukin–1β Enzyme," *Science 256*: 97–100, 1994.

Fernandes–Alnemri et al., "CPP32, A Novel Human Apoptotic Protein with Homology to *Caenorhabditis elegans* Cell Death Protein Ced–3 and Mammalian Interleukin–1–β–converting Enzyme," *J. Biol. Chem. 269*: 30761–30764, 1994.

Fisher, "Apoptosis in Cancer Therapy: Crossing the Threshold," *Cell 78*: 539–542, 1994.

Kumar et al., "Induction of Apoptosis by the Mouse Nedd2 Gene, Which Encodes a Protein Similar to the Product of the Caenorhabditis Enzyme," *Genes & Development 8*: 1613–1626, 1994.

Lazebnik et al., "Cleavage of Poly(ADP–ribose) Polymerase by a Proteinase With Properties Like ICE," *Nature 371*: 346–347, 1994.

Li et al., "Mice Deficient in 1L–1β and Resistant to Endotoxic Shock," *Cell 80*: 401–411, 1995

Thompson et al., "Apoptosis in the Genesis and Prevention of Cancer," *Cancer Epidem. Biomark. Preven. 1*: 597–602, 1992.

Thornberry et al., "Incactivation of interleukin–1β Converting Enzyme by Peptide (Acyloxymethyl) Ketones," *Biochemistry 33*: 3934–3940, 1994

Thornberry et al., "A Novel Heterodimeric Cysteine Protease is Required for Interleukin–1β Processing in Monocytes," *Nature 356*: 768–774, 1992.

Ulrich et al., "Insulin–like Growth Factor I Receptor Primary Structures: Comparison with Insulin Receptor Suggests Structural Determinants that Define Functional Specificity," *EMBO J. 5*(10): 2503–2512, 1986.

Walker et al., "Crystal Structure of the Cysteine Protease Interleukin 1β–converting Enzyme: A(p20/p10) 2 Homodimer," *Cell 78*: 343–352, 1994.

Wang et al., "Ich–1, an Ice/ced–3–related Gene, Encodes Both Positive and Negative Regulators of Programmed Cell Death," *Cell 78*: 739–750, 1994.

Wilson et al., "Structural and Mechanism of Interleukin–1β Converting Enzyme," *Nature 370*: 270–275, 1994.

Yuan et al., "The *C. elegans* Cell Death Gene ced–3 Encodes a Protein Similar to Mammalian Interleukin–1β–converting Enzyme," *Cell 75*: 641–652, 1993.

*Primary Examiner*—Johnny F. Railey, II
*Attorney, Agent, or Firm*—Seed and Berry LLP

[57] ABSTRACT

A substantially pure protein that is a member of the apoptotic Ced-3/Ice cysteine protease gene family, Mch2α, and an inactive isoform of it, Mch2β, are disclosed. Isolated nucleic acid molecules that encode Mch2α and Mch2β, respectively, are disclosed. Pharmaceutical compositions comprising a pharmaceutically acceptable carrier in combination with the protein or the nucleic acid molecules are disclosed. Fragments of nucleic acid molecules that encode Mch2α and Mch2β having at least 10 nucleotides and oligonucleotide molecule comprising a nucleotide sequence complimentary to a nucleotide sequence of at least 10 nucleotides are disclosed. Recombinant expression vectors that comprise the nucleic acid molecule that encode Mch2α or Mch2β, and host cells that comprise such recombinant vectors are disclosed. Antibodies that bind to an epitope on Mch2α and/or Mch2β are disclosed. Methods of identifying inhibitors, activators and substrates of Mch2α are disclosed. Antisense compounds and methods of using the same are disclosed.

2 Claims, No Drawings

MCH2, AN APOPTOTIC CYSTEINE PROTEASE, AND COMPOSITIONS FOR MAKING AND METHODS OF USING THE SAME

This application is a divisional of U.S. patent application Ser. No. 08/896,885, filed Jul. 18, 1997, which is a continuation of U.S. application Ser. No. 08/446,925, filed May 18, 1995, issued as U.S. Pat. No. 5,672,500.

ACKNOWLEDGEMENT OF GOVERNMENT RIGHTS

This invention was made with Government support under Grant A1 35035-01 from the National Institutes of Health. The Government has certain rights in this invention.

FIELD OF THE INVENTION

The invention relates to the identification and cloning of Mch2, a new member of the apoptotic Ced-3/Ice cysteine protease gene family and to methods of making and using the same.

BACKGROUND OF THE INVENTION

Several members of a new class of cysteine protease genes have been discovered recently as regulators of programmed cell death or apoptosis. These genes include mammalian Ice, Ich-1 (Nedd2) and Cpp32 (Mch1) genes as well as the *C. elegans* Ced-3 cell death gene. Except for ICE, the protein structure of Ich-1, Cpp32, or Ced-3 has not yet been determined. However, based on structural homology, these enzymes have a similar and unique structure that is unrelated to classical cysteine proteases. They all contain an active site QACRG (SEQ ID NO:1) pentapeptide. Furthermore, structural analysis suggests that these enzymes are synthesized as inactive proenzymes. The proenzymes are activated by proteolytic cleavage at conserved aspartic acid cleavage sites to generate two polypeptide subunits. In ICE, these subunits are known as p20 and p10 subunits that associate with each other to form the active heteromeric complex.

Apoptotic cell death is essential for normal development and maintenance of normal tissue size homeostasis in multicellular organisms. There is growing evidence that dysregulation of apoptosis may lead to several human diseases including cancer and degenerative neuronal diseases such as Alzheimer's and Parkinson's diseases. Therefore, it is probable that ICE-like cysteine proteases play a significant role in the pathogenesis of these diseases.

There is a need to identify members of the apoptotic Ced-3/Ice cysteine protease gene family. There is a need for isolated members of the apoptotic Ced-3/Ice cysteine protease gene family, and for compositions and methods of producing and isolating members of the apoptotic Ced-3/Ice cysteine protease gene family. There is a need to isolated proteins that are members of the apoptotic Ced-3/Ice cysteine protease gene family. There is a need to isolated nucleic acid molecules that encode members of the apoptotic Ced-3/Ice cysteine protease gene family. There is a need for compounds which inhibit activity of members of the apoptotic Ced-3/Ice cysteine protease gene family. There is a need for kits and methods of identifying such compounds.

SUMMARY OF THE INVENTION

The invention relates to substantially pure proteins that have amino acid sequences shown in SEQ ID NO:5 or SEQ ID NO:7.

The invention relates to pharmaceutical compositions comprising a protein that has the amino acid sequence shown in SEQ ID NO:5 or SEQ ID NO:7 in combination with a pharmaceutically acceptable carrier.

The invention relates to isolated nucleic acid molecules that comprise nucleic acid sequences that encode a protein that has an amino acid sequence shown in SEQ ID NO:5 or SEQ ID NO:7.

The invention relates to pharmaceutical compositions that comprise nucleic acid molecule that comprise nucleic acid sequences that encode a protein that has an amino acid sequence shown in SEQ ID NO:5 or SEQ ID NO:7 in combination with a pharmaceutically acceptable carrier.

The invention relates to isolated nucleic acid molecules that consist of SEQ ID NO:4 or SEQ ID NO:6 or a fragment thereof having at least 5 nucleotides.

The invention relates to a recombinant expression vector comprising the nucleic acid molecule that has a nucleotide sequence that comprises SEQ ID NO:4 or SEQ ID NO:6.

The invention relates to a host cell comprising a recombinant expression vector comprising the nucleic acid molecule that has a nucleotide sequence that comprises SEQ ID NO:4 or SEQ ID NO:6.

The invention relates to an oligonucleotide molecule comprising a nucleotide sequence complimentary to a nucleotide sequence of at least 5 nucleotides of SEQ ID NO:4 or SEQ ID NO:6.

The invention relates to isolated antibodies that bind to an epitope on SEQ ID NO:5 and/or SEQ ID NO:7.

The invention relates to methods of identifying substrates, activators or inhibitors of Mch2α.

The invention relates to methods of inhibiting expression of Mch2 by contacting cells that express Mch2 with a nucleic acid molecule that comprises an antisense nucleotide sequence that prevents transcription of Mch2 gene sequences or translation of Mch2 mRNA.

DETAILED DESCRIPTION OF THE INVENTION

A PCR technique was developed to isolate and characterize novel cysteine proteases. DNA sequences that encode the highly conserved amino acid sequences present in ICE-like apoptotic cysteine proteases are amplified using PCR primers designed based on specific sequences associated with such proteases. The cloning strategy utilized degenerate oligonucleotides encoding the highly conserved pentapeptides QACRG (SEQ ID NO:1) and GSWFI (SEQ ID NO:2) that are present in all known apoptotic cysteine proteases. PCR was performed using mRNA from human Jurkat T-lymphocytes. The new gene encodes a ~34 kDa protein that is highly homologous to human Cpp32, *C. elegans* cell death protein CED-3, mammalian Ice-1 (Nedd2) and mammalian interleukin-1 β converting enzyme (ICE). Because of its high homology to *C. elegans* Ced-3 gene, the new gene mammalian Ced-3 homolog was named Mch2 and comprises two isoforms.

Mch2 mRNA has been detected in total cellular RNA isolated from the following human tumor cell lines: Peer, SupT1, CEM C7, CEM C1, Molt4, and Jurkat, T-lymphocytes; 697, and 380, pre-B lymphocytes; K562, a promyelocyte; HeLa, a cervical carcinoma; A431, a vulva carcinoma; Colo320, a colon adenocarcinoma; MCF7, a breast carcinoma; A173, a glioblastoma; 293, an Ad-5-transformed embryonic kidney fibroblast.

Two Mch2 transcripts (Mch2α=1.7 kb and Mch2β=1.4 kb) were detected in Jurkat T-lymphocytes and other cell lines. The Mch2α transcript is believed to encode the full length Mch2 whereas the Mch2β transcript is believed to encode a shorter Mch2 isoform, probably as a result of alternative splicing.

Like ICE and Cpp32, recombinant Mch2α, but not Mch2β, possesses protease activity as determined by its ability to cleave the fluorogenic peptide DEVD-AMC (SEQ ID NO:3). Mch2 and CPP32 can also cleave poly(ADP-ribose) (PARP) in vitro suggesting that these enzymes participate in PARP cleavage observed during cellular apoptosis. In addition, overexpression of recombinant Mch2α, but not Mch2β, induces rapid apoptosis in Sf9 insect cells. Based upon these data, Mch2 has been characterized as a Ced-3/ICE-like cysteine protease and a candidate mediator of apoptosis in mammalian cells.

The discovery of Mch2 and its two isoforms provides the means to design and discover specific inhibitors, activators and substrates of this apoptotic cysteine protease. According to the present invention, Mch2α may be used to screen compounds for inhibitors, activators or substrates. Inhibitors are useful as anti-apoptotic agents. Activators are useful as apoptotic agents that have cytotoxic effects such as anti-tumor activity. Substrates are useful as reagents in assays to identify inhibitors and activators. Kits are provided for screening compounds for Mch2α inhibitors. Kits are provided for screening compounds for Mch2α activators. Kits are provided for screening compounds for Mch2α substrates. The nucleotide sequences that encode the Mch2 isoforms are disclosed herein and allow for the production of pure protein, the design of probes which specifically hybridize to nucleic acid molecules that encode the Mch2 isoforms and antisense compounds to inhibit transcription of Mch2 isoforms. Anti-Mch2α and anti-Mch2β antibodies are provided. Anti-Mch2α antibodies may be inhibitors of Mch2α and may be used in methods of isolating pure Mch2 and methods of inhibiting Mch2α activity. Anti-Mch2β antibodies may be inhibitors of Mch2β and may be used in methods of isolating pure Mch2 and methods of inhibiting Mch2β activity.

The present invention provides substantially purified Mch2 isoforms Mch2α and Mch2β which have amino acid sequences consisting of: SEQ ID NO:5 and SEQ ID NO:7, respectively. Mch2 isoforms Mch2α and Mch2β can be isolated from natural sources, produced by recombinant DNA methods or synthesized by standard protein synthesis techniques.

Antibodies which specifically bind to a particular Mch2 isoform may be used to purify the protein from natural sources using well known techniques and readily available starting materials. Such antibodies may also be used to purify the Mch2 isoform from material present when producing the protein by recombinant DNA methodology. The present invention relates to antibodies that bind to an epitope which is present on an Mch2 isoform selected from the group consisting of: Mch2α—SEQ ID NO: 5 and Mch2β—SEQ ID NO: 7. As used herein, the term "antibody" is meant to refer to complete, intact antibodies, and Fab fragments and $F(ab)_2$ fragments thereof. Complete, intact antibodies include monoclonal antibodies such as murine monoclonal antibodies, chimeric antibodies and humanized antibodies. In some embodiments, the antibodies specifically bind to an epitope of only one of: Mch2α—SEQ ID NO:5 and Mch2β—SEQ ID NO:7. Antibodies that bind to an epitope which is present on an Mch2 isoform are useful to isolate and purify the Mch2 isoform from both natural sources or recombinant expression systems using well known techniques such as affinity chromatography. Such antibodies are useful to detect the presence of such protein in a sample and to determine if cells are expressing the protein.

The production of antibodies and the protein structures of complete, intact antibodies, Fab fragments and $F(ab)_2$ fragments and the organization of the genetic sequences that encode such molecules are well known and are described, for example, in Harlow, E. and D. Lane (1988) *ANTIBODIES: A Laboratory Manual,* Cold Spring Harbor Laboratory, Cold Spring Harbor, N.Y. which is incorporated herein by reference. Briefly, for example, the Mch2 isoform protein, or an immunogenic fragment thereof is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the Mch2 isoform, the hybridoma which produces them is cultured to produce a continuous supply of antibodies.

Using standard techniques and readily available starting materials, a nucleic acid molecule that encodes each of the Mch2 isoform may be isolated from a cDNA library, using probes or primers which are designed using the nucleotide sequence information disclosed in SEQ ID NO:4 or SEQ ID NO:6. The present invention relates to an isolated nucleic acid molecule that comprises a nucleotide sequence that encodes an Mch2 isoform selected from the group consisting of Mch2α and Mch2β that comprises the amino acid sequence of SEQ ID NO:5, and SEQ ID NO:7, respectively. In some embodiments, the nucleic acid molecules consist of a nucleotide sequence that encodes Mch2α or Mch2β. In some embodiments, the nucleic acid molecules comprise the nucleotide sequence that consists of the coding sequence in SEQ ID NO:4 or SEQ ID NO:6. In some embodiments, the nucleic acid molecules consist of the nucleotide sequence set forth in SEQ ID NO:4 or SEQ ID NO:6. The isolated nucleic acid molecules of the invention are useful to prepare constructs and recombinant expression systems for preparing the Mch2 isoforms of the invention.

A cDNA library may be generated by well know techniques. A cDNA clone which contains one of the nucleotide sequences set out is identified using probes that comprise at least a portion of the nucleotide sequence disclosed in SEQ ID NO:4 or SEQ ID NO:6. The probes have at least 16 nucleotides, preferably 24 nucleotides. The probes are used to screen the cDNA library using standard hybridization techniques. Alternatively, genomic clones may be isolated using genomic DNA from any human cell as a starting material. The present invention relates to isolated nucleic acid molecules that comprise a nucleotide sequence identical or complementary to a fragment of SEQ ID NO:4 or SEQ ID NO:6 which is at least 10 nucleotides. In some embodiments, the isolated nucleic acid molecules consist of a nucleotide sequence identical or complementary to a fragment of SEQ ID NO:4 or SEQ ID NO:6 which is at least 10 nucleotides. In some embodiments, the isolated nucleic acid molecules comprise or consist of a nucleotide sequence identical or complementary to a fragment of SEQ ID NO:4 or SEQ ID NO:6 which is 15–150 nucleotides. In some embodiments, the isolated nucleic acid molecules comprise or consist of a nucleotide sequence identical or complementary to a fragment of SEQ ID NO:4 or SEQ ID NO:6 which is 15–30 nucleotides. Isolated nucleic acid molecules that comprise or consist of a nucleotide sequence identical or complementary to a fragment of SEQ ID NO:4 or SEQ ID NO:6 which is at least 10 nucleotides are useful as probes for identifying genes and cDNA sequence having SEQ ID NO:4 or SEQ ID NO:6, respectively, PCR primers for amplifying genes and cDNA having SEQ ID NO:4 or SEQ ID NO:6, respectively, and antisense molecules for inhibiting transcription and translation of genes and cDNA, respectively, which encode Mch2 isoforms having the amino acid sequence of SEQ ID NO:5 or SEQ ID NO:7, respectively.

The cDNA that encodes an Mch2 isoform may be used as a molecular marker in electrophoresis assays in which cDNA from a sample is separated on an electrophoresis gel and Mch2 isoform probes are used to identify bands which hybridize to such probes. Specifically, SEQ ID NO:4 or portions thereof, or SEQ ID NO:6 or portions thereof, may be used as a molecular marker in electrophoresis assays in which cDNA from a sample is separated on an electrophoresis gel and Mch2 isoform specific probes are used to identify bands which hybridize to them, indicating that the band has a nucleotide sequence complementary to the sequence of the probes. The isolated nucleic acid molecule provided as a size marker will show up as a positive band which is known to hybridize to the probes, and thus can be used as a reference point to the size of cDNA that encodes Mch2α and Mch2β, respectively. Electrophoresis gels useful in such an assay include standard polyacrylamide. gels as described in Sambrook et al., *Molecular Cloning a Laboratory Manual,* Second Ed. Cold Spring Harbor Press (1989) which is incorporated herein by reference.

The nucleotide sequences in SEQ ID NO:4 and SEQ ID NO:6 may be used to design probes, primers and complimentary molecules which specifically hybridize to the unique nucleotide sequences of Mch2α and Mch2β, respectively. Probes, primers and complimentary molecules which specifically hybridize to nucleotide sequence that encodes Mch2α and Mch2β may be designed routinely by those having ordinary skill in the art.

The present invention also includes labelled oligonucleotides which are useful as probes for performing oligonucleotide hybridization methods to identify Mch2α and Mch2β. Accordingly, the present invention includes probes that can be labelled and hybridized to unique nucleotide sequences of Mch2α and Mch2β. The labelled probes of the present invention are labelled with radiolabelled nucleotides or are otherwise detectable by readily available nonradioactive detection systems. In some preferred embodiments, probes comprise oligonucleotides consisting of between 10 and 100 nucleotides. In some preferred, probes comprise oligonucleotides consisting of between 10 and 50 nucleotides. In some preferred, probes comprise oligonucleotides consisting of between 12 and 20 nucleotides. The probes preferably contain nucleotide sequence completely identical or complementary to a fragment of a unique nucleotide sequences of Mch2α and Mch2β.

PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inca San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. Some simple rules aid in the design of efficient primers. Typical primers are 18–28 nucleotides in length having 50% to 60% g+c composition. The entire primer is preferably complementary to the sequence it must hybridize to. Preferably, primers generate PCR products 100 basepairs to 2000 base pairs. However, it is possible to generate products of 50 base pairs to up to 10 kb and more.

PCR technology allows for the rapid generation of multiple copies of nucleotide sequences by providing 5' and 3' primers that hybridize to sequences present in a nucleic acid molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the complementary strands of the same fragment of nucleic acid, exponential amplification of a specific double-stranded product results. If only a single primer hybridizes to the nucleic acid molecule, linear amplification produces single-stranded products of variable length.

One having ordinary skill in the art can isolate the nucleic acid molecule that encode Mch2α or Mch2β and insert it into an expression vector using standard techniques and readily available starting materials.

The present invention relates to a recombinant expression vector that comprises a nucleotide sequence that encodes Mch2α or Mch2β that comprises the amino acid sequence of SEQ ID NO:5 or SEQ ID NO:7, respectively. As used herein, the term "recombinant expression vector" is meant to refer to a plasmid, phage, viral particle or other vector which, when introduced into an appropriate host, contains the necessary genetic elements to direct expression of the coding sequence that encodes the Mch2 isoforms of the invention. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. In some embodiments, the recombinant expression vector comprises the nucleotide sequence set forth in SEQ ID NO:4 or SEQ ID NO:6. The recombinant expression vectors of the invention are useful for transforming hosts to prepare recombinant expression systems for preparing the Mch2 isoforms of the invention.

The present invention relates to a host cell that comprises the recombinant expression vector that includes a nucleotide sequence that encodes an Mch2 isoform that comprises SEQ ID NO:5 or SEQ ID NO:7. In some embodiments, the host cell comprises a recombinant expression vector that comprises SEQ ID NO:4 or SEQ ID NO: 6. Host cells for use in well known recombinant expression systems for production of proteins are well known and readily available. Examples of host cells include bacteria cells such as *E. coli,* yeast cells such as *S. cerevisiae,* insect cells such as *S. frugiperda,* non-human mammalian tissue culture cells chinese hamster ovary (CHO) cells and human tissue culture cells such as HeLa cells.

The present invention relates to a transgenic non-human mammal that comprises the recombinant expression vector that comprises a nucleic acid sequence that encodes the Mch2 isoform that comprises the amino acid sequence of SEQ ID NO:5. or SEQ ID NO:7. Transgenic non-human mammals useful to produce recombinant proteins are well known as are the expression vectors necessary and the techniques for generating transgenic animals. Generally, the transgenic animal comprises a recombinant expression vector in which the nucleotide sequence that encodes an Mch2 isoform of the invention is operably linked to a mammary cell specific promoter whereby the coding sequence is only expressed in mammary cells and the recombinant protein so expressed is recovered from the animal's milk. In some embodiments, the coding sequence that encodes an Mch2 isoform is SEQ ID NO:4 or SEQ ID NO:6.

In some embodiments, for example, one having ordinary skill in the art can, using well known techniques, insert such DNA molecules into a commercially available expression vector for use in well known expression systems. For example, the commercially available plasmid pSE420 (Invitrogen, San Diego, Calif.) may be used for production of collagen in *E. coli.* The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I (Invitrogen, San Diego, Calif.) may, for example, be used for production in mammalian cells such as Chinese Hamster Ovary cells. One having ordinary skill in the art can use these commercial expression vectors and systems or others to produce an Mch2 isoform of the invention using routine techniques and readily available starting materials. (See e.g., Sambrook et al., *Molecular Cloning, a Laboratory Manual,* Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual,* Second Ed. Cold Spring Harbor Press (1989).

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but is not limited to, yeast, fungal cells, insect cells, mammalian cells, avian cells, and cells of higher plants. Suitable promoters are available which are compatible and operable for use in each of these host types as well as are termination sequences and enhancers, e.g. the baculovirus polyhedron promoter. As above, promoters can be either constitutive or inducible. For example, in mammalian systems, the mouse metallothionein promoter can be induced by the addition of heavy metal ion.

The particulars for the construction of expression systems suitable for desired hosts are known to those in the art. Briefly, for recombinant production of the protein, the DNA encoding the polypeptide is suitably ligated into the expression vector of choice. The DNA is operably linked to all regulatory elements which are necessary for expression of the DNA in the selected host. One having ordinary skill in the art can, using well known techniques, prepare expression vectors for recombinant production of the polypeptide.

The expression vector including the DNA that encodes the Mch2 isoform is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. One having ordinary skill in the art can, using well known techniques, isolate the Mch2 isoform that is produced using such expression systems. The methods of purifying Mch2 isoforms from natural sources using antibodies which specifically bind to the Mch2 isoform as described above, may be equally applied to purifying Mch2 isoforms produced by recombinant DNA methodology.

Examples of genetic constructs include the Mch2 isoform coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes Mch2 isoform from readily available starting materials. Such gene constructs are useful for the production of the Mch2 isoform.

In some embodiments of the invention, transgenic non-human animals are generated. The transgenic animals according to the invention contain SEQ ID NO:4 or SEQ ID NO:6 under the regulatory control of a mammary specific promoter. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which produce the Mch2 isoform. Preferred animals are rodents, particularly goats, rats and mice.

In addition to producing these proteins by recombinant techniques, automated peptide synthesizers may also be employed to produce Mch2 isoforms of the invention. Such techniques are well known to those having ordinary skill in the art and are useful if derivatives which have substitutions not provided for in DNA-encoded protein production.

Mch2β is inactive. Mch2 activity may be regulated this way, i.e. Mch2β may compete with Mch2α and increased levels of Mch2β may reduce overall Mch2 activity. The biological significance of the expression of an alternatively spliced Mch2 isoform is realized from its ability to modulate Mch2 activity.

Accordingly, Mch2β may be used as a pharmaceutical to inhibit Mch2β activity which is involved in apoptosis. Similarly, nucleic acid molecules that encode Mch2β may be used as part of pharmaceutical compositions for gene therapy. Diseases characterized by apoptosis include HIV infection and Alzheimer's disease. Those having ordinary skill in the art can readily identify individuals who are suspected of suffering from such diseases, conditions and disorders using standard diagnostic techniques.

Mch2α may be used as a pharmaceutical to induce apoptosis in cells whose elimination is desirable. Similarly, nucleic acid molecules that encode Mch2α may be used as part of pharmaceutical compositions for gene therapy. Diseases in which cell elimination by induction of apoptosis include cancer and autoimmune disease. Those having ordinary skill in the art can readily identify individuals who are suspected of suffering from such diseases, conditions and disorders using standard diagnostic techniques.

Pharmaceutical compositions according to the invention comprise a pharmaceutically acceptable carrier in combination with Mch2α or Mch2β. Pharmaceutical formulations are well known and pharmaceutical compositions comprising Mch2α or Mch2β may be routinely formulated by one having ordinary skill in the art. Suitable pharmaceutical carriers are described in *Remington's Pharmaceutical Sciences,* A. Osol, a standard reference text in this field, which is incorporated herein by reference. The present invention relates to an injectable pharmaceutical composition that comprises a pharmaceutically acceptable carrier and Mch2α or Mch2β. Some embodiments of the invention relate to injectable pharmaceutical compositions that comprise a pharmaceutically acceptable carrier and amino acid sequence SEQ ID NO:5 or SEQ ID NO:7. Mch2α or Mch2β is preferably sterile and combined with a sterile pharmaceutical carrier.

In some embodiments, for example, Mch2α or Mch2β can be formulated as a solution, suspension, emulsion or lyophilized powder in association with a pharmaceutically acceptable vehicle. Examples of such vehicles are water, saline, Ringer's solution, dextrose solution, and 5 human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

An injectable composition may comprise Mch2α or Mch2β in a diluting agent such as, for example, sterile water, electrolytes/dextrose, fatty oils of vegetable origin, fatty esters, or polyols, such as propylene glycol and polyethylene glycol. The injectable must be sterile and free of pyrogens.

Nucleic acid molecules that encode Mch2α or Mch2β may be delivered using any one of a variety of delivery components, such as recombinant viral expression vectors or other suitable delivery means, so as to affect their introduction and expression in compatible host cells. In general, viral vectors may be DNA viruses such as recombinant adenoviruses and recombinant vaccinia viruses or RNA viruses such as recombinant retroviruses. Other recombinant vectors include recombinant prokaryotes which can infect cells and express recombinant genes. In addition to recombinant vectors, other delivery components are also contemplated such as encapsulation in liposomes, transferrin-mediated transfection and other receptor-mediated means. The invention is intended to include such other forms of expression vectors and other suitable delivery means which serve equivalent functions and which become known in the art subsequently hereto.

In one embodiment of the present invention, DNA is delivered to competent host cells by means of an adenovirus. One skilled in the art would readily understand this technique of delivering DNA to a host cell by such means. Although the invention preferably includes adenovirus, the invention is intended to include any virus which serves equivalent functions.

In another embodiment of the present invention, RNA is delivered to competent host cells by means of a retrovirus. One skilled in the art would readily understand this technique of delivering RNA to a host cell by such means. Any retrovirus which serves to express the protein encoded by the RNA is intended to be included in the present invention.

In another embodiment of the present invention, nucleic acid is delivered through folate receptor means. The nucleic acid sequence to be delivered to a cell is linked to polylysine and the complex is delivered to cells by means of the folate receptor. U.S. Pat. No. 5,108,921 issued Apr. 28, 1992 to Low et al., which is incorporated herein by reference, describes such delivery components.

Pharmaceutical compositions according to the invention include delivery components in combination with nucleic acid molecules that encode Mch2α or Mch2β which further comprise a pharmaceutically acceptable carriers or vehicles, such as, for example, saline. Any medium may be used which allows for successful delivery of the nucleic acid. One skilled in the art would readily comprehend the multitude of pharmaceutically acceptable media that may be used in the present invention.

The pharmaceutical compositions of the present invention may be administered by any means that enables the active agent to reach the agent's site of action in the body of a mammal. Pharmaceutical compositions may be administered parenterally, i.e., intravenous, subcutaneous, intramuscular. Intravenous administration is the preferred route.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired.

According to one aspect of the invention, compounds; may be screened to identify Mch2α inhibitors, activators or substrates. Inhibitors of Mch2α are useful as anti-apoptotic agents. Activators of Mch2α are useful as cytotoxic agents. Substrates of Mch2α are useful as reagents in assays for screening compounds with Mch2α activity.

Inhibitors of Mch2α may be identified by screening compounds to ascertain their effect on Mch2α activity. In some embodiments of the invention, compounds are screened to identify inhibitors by delivering Mch2α to cells in the presence or absence of a test compound. Under assay conditions, the cells will become apoptotic in the absence of test compound. If in the presence of the test compound, the cells do not become apoptotic, the test compound is candidate inhibitor of Mch2α. Antibodies which inhibit the Mch2α activity are useful as inhibitors and, therefore as positive controls in the assay. In some embodiments, the Mch2α is delivered to the cell as a protein. In some embodiments, the Mch2α is delivered to the cell as a nucleic acid molecule that encodes the protein. In some embodiments of the invention, compounds are screened to identify inhibitors by contacting Mch2α to a substrate in the presence or absence of a test compound. Under assay conditions, the substrate is cleaved in the absence of test compound. If the substrate is not processed in the presence of the test compound but is processed under the negative control condition in which the test compound is absent, the test compound is an inhibitor of Mch2α. Those having ordinary skill in the art can readily detect whether or not substrate has been processed. Antibodies which inhibit the Mch2α activity are useful as inhibitors and, therefore as positive controls in the assay.

Activators of Mch2α may be identified by screening compounds to ascertain their effect on Mch2α activity. In some embodiments of the invention, compounds are screened to identify activators by delivering Mch2α to cells in the presence or absence of a test compound. Under assay conditions, the cells will become apoptotic in the absence of test compound. If in the presence of the test compound, apoptotic activity is enhanced, magnified or accelerated, the test compound is candidate activator of Mch2α. In some embodiments, the Mch2α is delivered to the cell as a protein. In some embodiments, the Mch2α is delivered to the cell as a nucleic acid molecule that encodes the protein. In some embodiments of the invention, compounds are screened to identify activators by contacting Mch2α to a substrate in the presence or absence of a test compound. Under assay conditions, the substrate is cleaved in the absence of test compound. If the substrate is processed faster or more efficiently in the presence of the test compound compared to the level of processing that occurs under the control condition in which the test compound is absent, the test compound is an activator of Mch2α. Those having ordinary skill in the art can readily detect the rate that a substrate has been processed.

As used herein, the term substrate is meant to refer to a peptide which will be cleaved by Mch2α. Examples of substrates include the ICE fluorogenic peptide substrate DEVD-AMC (SEQ ID NO:3) or a peptide which shares the proteolytic, cleavage site of the fluorogenic peptide substrate DEVD-AMC (SEQ ID NO:3) and will be cleaved by Mch2α. The present invention may include methods and kits for identifying other substrates which can be processed by Mch2α. Those having ordinary skill in the art can readily identify substrates which are processed.

In some embodiments of the invention, the preferred concentration of test compound is between 1 μM and 500 μM. A preferred concentration is 10 μM to 100 μM. In some preferred embodiments, it is desirable to use a series of dilutions of test compounds.

Kits are included which comprise containers with reagents necessary to screen test compounds. Such kits include Mch2α and/or a nucleic acid molecule that encodes Mch2α, and instructions for performing the assay. Kits may include cells, or a substrate such as the fluorogenic peptide substrate DEVD-AMC (SEQ ID NO:3) and a means to distinguish processed substrate from uncleaved substrate. Optionally Mch2β and/or a nucleic acid molecule that encodes Mch2β is provided as a control and/or anti-Mch2α antibodies are provided as a control.

The means for distinguishing processed substrate from uncleaved substrate include, for example, antibodies which bind to processed substrate but not uncleaved substrate, antibodies which bind to uncleaved substrate but not processed substrate, and liberation assay reagents in labelled uncleaved substrate is bound to solid phase and upon processing of the substrate by the enzyme the label is liberated from the solid phase at which time it is either detected as unbound or its absence is detected from the bound material. Those of ordinary skill in the art can readily design kits to practice the assays of the invention and measure the capacity of test compounds to inhibit Mch2α activity. Inhibitors are useful as anti-apoptotic agents. Activators are useful as apoptotic agents.

According to another aspect of the invention, transgenic animals, particularly transgenic mice, are generated. In some embodiments, the transgenic animals according to the invention contain a nucleic acid molecule which encodes Mch2. Such transgenic mice may be used as animal models for studying overexpression of Mch2 and for use in drug evaluation and discovery efforts to find compounds effective to inhibit or modulate the activity of Mch2. One having ordinary skill in the art using standard techniques, such as those taught in U.S. Pat. No. 4,873,191 issued Oct. 10, 1989 Wagner and U.S. Pat. No. 4,736,866 issued Apr. 12, 1988 to Leder, both of which are incorporated herein by reference, can produce transgenic animals which produce the Mch2 and use the animals in drug evaluation and discovery projects.

Another aspect of the present invention relates to knockout mice and methods of using the same. In particular, transgenic mice may be generated which are homologous for a mutated, non-functional Mch2 gene which is introduced into them using well known techniques. The mice produce no functional Mch2 and are useful to study the function of Mch2. Furthermore, the mice may be used in assays to study the effect: of test compounds on Mch2 deficiency. The Mch2 deficient mice can be used to determine if, how and to what extent Mch2 inhibitors will effect the animal and thereby address concerns associated with inhibiting the activity of the molecule.

Methods of generating genetically deficient "knock out" mice are well known and disclosed in Capecchi, M. R. (1989) *Science* 244:1288–1292 and Li, P. et al. (1995) *CELL* 80:401–411, which are each incorporated herein by reference. The human Mch2 cDNA clone can be used to isolate a murine Mch2 genomic clone. The genomic clone can be used to prepare a Mch2 targeting construct which can disrupt the Mch2 gene in the mouse by homologous recombination.

The targeting construct contains a non-functioning portion of the Mch2 gene which inserts in place of the functioning portion of the native mouse gene. The non-functioning insert generally contains an insertion in the exon that encodes the active region of Mch2. The targeting construct can contain markers for both positive and negative selection. The positive selection marker allows for the selective elimination of cells without it while the negative selection marker allows for the elimination of cells that carry it.

For example, a first selectable marker is a positive marker that will allow for the survival of cells carrying it. In some embodiments, the first selectable marker is an, antibiotic resistance gene such as the neomycin resistance gene can be placed within the coding sequences of the Mch2 gene to render it non-functional while additionally rendering the construct selectable. The antibiotic resistance gene is within the homologous region which can recombine with native sequences. Thus, upon homologous reconstruction, the non-functional and antibiotic resistance selectable gene sequences will be taken up.

The targeting construct also contains a second selectable marker which is a negative selectable marker. Cells with the negative selectable marker will be eliminated. The second selectable marker is outside the recombination region. Thus, if the entire construct is present in the cell, both markers will be present. If the construct has recombined with native sequences, the first selectable marker will be incorporated into the genome and the second will be lost. The herpes simplex virus thymidine kinase (HSV tk) gene is an example of a negative selectable marker which can be used as a second marker to eliminate cells that carry it. Cells with the HSV tk gene are selectively killed in the presence of gangcyclovir.

Cells are transfected with targeting constructs and then selected for the presence of the first selection marker and the absence of the second. Clones are then injected into the blastocysts and implanted into pseudopregnant females. Chimeric offspring which are capable of transferring the recombinant genes in their germline are selected, mated and their offspring is examined for heterozygous carriers of the recombined genes. Mating of the heterozygous offspring can then be used to generate fully homozygous offspring which are the Mch2-deficient knock out mouse.

The present invention relates to methods of and compositions for inhibiting the expression of Mch2 in cells. In one embodiment, antisense oligonucleotides are provided which have a nucleotide sequence complementary to a nucleotide sequence of mRNA that encodes Mch2.

The antisense oligonucleotides of the present invention comprise sequences complementary to regions of Mch2 mRNA. The oligonucleotides comprise a sequence complementary to a region selected from the sequence of Mch2 mRNA. The antisense oligonucleotides include single stranded DNA sequence and an antisense RNA oligonucleotide produced from an expression vector. Each of the antisense oligonucleotides of the present invention are complementary to regions of the Mch2 mRNA sequence.

The antisense oligonucleotides of the present invention comprises a sequence complementary to a fragment of SEQ ID NO:4 or SEQ ID NO:6. See Ullrich et al., *EMBO J.,* 1986, 5:2503, which is incorporated herein by reference. Contemplated by this definition are fragments of oligos within the coding sequence for Mch2. Oligonucleotides are preferably complementary to a nucleotide sequence that is 5–50 nucleotides in length, in some embodiments 8–40, more preferably 12–25 nucleotides, in some embodiments 10–15 nucleotides and in some embodiments 12–20 nucleotides.

In addition, mismatches within the sequences identified above, which achieve the methods of the invention, such that the mismatched sequences are substantially complementary to the Mch2 sequences are also considered within the scope of the disclosure. Mismatches which permit substantial complementarily to the Mch2 sequences will be known to those of skill in the art once armed with the present disclosure. The oligos may also be unmodified or modified.

The present invention is also directed to a method of inhibiting Mch2 expression in mammals comprising contacting the mammal with an effective amount of an antisense oligonucleotide having a sequence which is complementary to a region of the Mch2 mRNA.

Methods of administering the antisense oligos of the present invention include techniques well known in the art such as and not limited to liposomes, plasmid expression, or viral vector including retroviral vectors. In the administration of oligos via vectors or plasmids, a non-coding RNA strand of Mch2 is preferably used in order to produce antisense RNA oligos which are expressed by the cell. The RNA oligos then bind Mch2 sense or coding RNA sequence.

Methods of administering the oligos to mammals include liposomes, and may be in a mixture with a pharmaceutically-acceptable carrier, selected with regard to the intended route of administration and the standard pharmaceutical practice. In addition, antibodies, ligands and the like may be incorporated into the liposomes thereby providing various modes of inhibiting Mch2 expression. Dosages will be set with regard to weight, and clinical condition of the patient. The proportional ratio of active ingredient to carrier will naturally depend on the chemical nature, solubility, and stability of the compounds, as well as the dosage contemplated. The oligos of the present invention will be administered for a time sufficient for the mammals to be free of undifferentiated cells and/or cells having an abnormal phenotype.

The oligos of the invention may be employed in the method of the invention singly or in combination with other compounds. The amount to be administered will also depend on such factors as the age, weight, and clinical condition of the patient. See Gennaro, Alfonso, ed., Remington's Pharmaceutical Sciences, 18th Edition, 1990, Mack Publishing Co., Easton, Pa.

The compounds of the present invention may be administered by any suitable route, including inoculation and injection, for example, intravenous, oral, intraperitoneal, intramuscular, subcutaneous, topically, and by absorption through epithelial or mucocutaneous linings, for example, nasal, oral, vaginal, rectal and gastrointestinal.

The mode of administration of the oligos may determine the sites in the organism to which the compound will be delivered. For instance, topical application may be administered in creams, ointments, gels, oils, emulsions, pastes, lotions, and the like. The oligos of the present invention may be administered alone or will generally be administered in admixture with a pharmaceutical carrier selected with regard to the intended route of administration and standard pharmaceutical practice. For parenteral administration, they are best used in the form of sterile aqueous solution which may contain other solutes, for example, sufficient salts, glucose or dextrose to make the solution isotonic. For oral mode of administration, the present invention may be used in the form of tablets, capsules, lozenges, troches, powders, syrups, elixirs, aqueous solutions and suspension, and the like. Various disintegrants such as starch, and lubricating agents may be used. For oral administration in capsule form, useful diluents are lactose and high molecular weight polyethylene glycols. When aqueous suspensions are required for oral use, certain sweetening and/or flavoring agents may be added. Forty μg/ml antisense oligo was used for in vitro methods of providing oligos in media for cell growth in culture. This concentration may be extrapolated for in vivo use. The concentration of antisense oligonucleotides for in vivo use is about 40 μ/g body weight. The in vivo use of the expression vector expressing RNA oligonucleotides is determined by the number of transfected cells.

For in vivo use, the antisense oligonucleotide may be combined with a pharmaceutically acceptable carrier, such as suitable liquid vehicle or excipient and an optional auxiliary additive or additives. The liquid vehicles and excipients are conventional and commercially available. Illustrative thereof are distilled water, physiological saline, aqueous solution of dextrose, and the like. For in vivo antineoplastic use, the antisense oligonucleotides may be administered intravenously.

In addition to administration with conventional carriers, antisense oligonucleotides may be administered by a variety of specialized oligonucleotide delivery techniques. For example, oligonucleotides have been successfully encapsulated in unilamellar liposomes. Reconstituted Sendai virus envelopes have been successfully used to deliver RNA and DNA to cells. Arad et al., *Biochem. Biophy. Acta.,* 1986, 859, 88–94.

EXAMPLE

Materials and Methods

Cloning of Mch2

Employing a PCR approach designed to identify and clone novel members of the Ced-3/ICE-like apoptotic cysteine proteases, a partial cDNA sequence was identified with high homology to CPP32 and Ced-3. The new partial cDNA was used as a probe to screen the original human Jurkat T-lymphocyte cDNA library. This resulted in the isolation of several cDNA clones. The sequences of two of these clones are shown in SEQ ID NO:4 and SEQ ID NO:6.

These two cDNAs are named mammalian Ced-3 homologs Mch2α and Mch2β. Mch2α contains an open reading frame of 879 bp that encodes a 293 amino acid protein with a predicted molecular mass of ~34 kDa. The initiator methionine at nucleotide 79 conforms to the consensus Kozak translation initiation sequence. Mch2β contains a deletion corresponding to nucleotides 119–385 of the Mch2α sequence (amino acids 14–102) and it has a longer 3' nontranslated sequence.

The deletion in Mch2β could be due to alternative splicing of the parental Mch2 mRNA. Mch2α contains an alternative splice donor/acceptor site within its coding sequence that conforms to the GT/AG rule (bp 119–385). This site is located exactly at the splice junction. Northern blot: analysis of the expression of Mch2 revealed two mRNA species of ~1.7 kb and ~1.4 kb in the human 380 pre-B lymphocytes and the human Jurkat T-lymphocytes. However, there appears to be a difference in the relative level of expression of each mRNA species in the two cell lines and these may be the two mRNA species correspond to Mch2α and Mch2β, respectively.

Mch2β cDNA maintained an open reading frame of 612 bp which encodes a 204 amino acid protein with a predicted molecular mass of ~23 kDa. Mch2β lacks approximately half of its putative p20 subunit and is probably inactive. The inactive isoform could regulate the activity of the parental enzyme by acting as a dominant inhibitor. Because active ICE-like cysteine proteases are generated by proteolytic cleavage followed by heterodimerization of their p20 and p10 subunits, inactive alternatively spliced isoforms could interfere with this process by forming inactive heteromeric complexes with the parental full length enzyme.

Mch2 is a Novel Ced/ICE-like Cysteine Protease

The predicted Mch2α protein sequence is similar to human CPP32, the *C. elegans* CED-3 protein, mammalian Ich-1 (NEDD2) and ICE proteins. The full length Mch2α protein shows the highest homology to CPP32. Overall, the two proteins share 38% identity and 56% similarity. However, like CPP32, Mch2α is more related to CED-3 than to the remaining cysteine proteases: Mch2α shows 35% identity (56% similarity) with CED-3, 29% identity (52% similarity) with human Ich-1 and 29% identity (52% similarity) with human ICE. CED-3, ICE or Ich-1 are less than 29% identical among each other. The predicted structure of Mch2α appears to be similar to ICE and CPP32. Proteolytic cleavage of Mch2α of Mch2α at Asp176, Asp179, Asp186 and/or Asp193 would generate two polypeptides equivalent to the p20 and p10 subunits of ICE and CPP32. Mch2α, like CPP32, lacks the long N-terminal propeptide present in other cysteine proteases. However, there are three potential aspartic acid cleavage site at positions 23, 32 and 40 that could be used to remove a short propeptide during processing of Mch2α to the active enzyme. Although Mch2α and CPP32 are equally related to Ced-3, the putative p20 subunit of Mch2α (amino acids 1–179) is more related to the putative p20 subunit of Ced-3 (36% identity) than to the putative p20 subunit of CPP32 (33% identity). Consequently, if the p20 subunit or its equivalent largely determines the enzyme specificity, then Mch2α is more functionally related to Ced-3 than to CPP32.

Expression and Autoprocessing of Mch2, CPP32 and ICE in *E. coli*

To determine the enzymatic activity of Mch2, CPP32 or ICE, these enzymes were expressed in *E. coli* as fusion proteins with glutathione S-transferase (GST). A GST-CPP32-p20 fusion protein that contains amino acids 1–175 of CPP32 and a GST nonfusion protein were used as controls. After induction with IPTG, bacterial extracts were prepared from *E. coli* expressing the recombinant fusion proteins. The extracts were absorbed to glutathione-Sepharose resin, washed several times and then analyzed by SDS-PAGE. The ICEγ, CPP32 and Mch2α preparations containing GST-fusion proteins ranged in size from ~28–35 kDa. The GST nonfusion protein control migrated as a ~27–28 kDa protein. Although the predicted molecular mass of GST-ICEγ fusion protein is ~61.5 kDa, two bands of ~28 kDa and ~31 kDa were seen in the ICEγ preparation. This suggests that ICEγ can autoprocess itself to generate active ICE by cleaving the N-terminal GST-propeptide at one of two Asp cleavage sites. Aps26 of ICEγ which corresponds to Asp 119 of ICEα is a site that is cleaved during ICE activation. Cleavage at this site would generate a GST-fusion protein with a predicted molecular mass of ~29 kDa that might correspond to the 31 kDa band. Cleavage at Asp 3 of ICEγ, although it is not a known ICE cleavage site, could generate the 28 kDa band (lane 2). Similar to the GST-ICEγ preparation, the GST-CPP32 and GST-Mch2 preparations contain smaller than predicted GST fusion products. The GST-CPP32 fusion product migrates as a ~29–30 kDa protein. Cleavage at Asp9 or Asp28 of CPP32 would generate products with predicted molecular masses of ~27.3 kDa or ~29.4 kDa, respectively. Based on the observed size of the GST-CPP32 product, CPP32 is most probably cleaved at Asp28, although it is possible that both sites are cleaved during CPP32 autoprocessing. Unlike the GST-CPP32 which contains full length CPP32, the GST-CPP32-p20 product which contains a truncated CPP32 migrates as a ~46 kDa protein that agreed with its predicted molecular mass. Because this recombinant protein lacks the p11 subunit (amino acids 176–277) it is inactive and does not autoprocess to generate the ~29–30 kDa GST-CPP32 cleavage product observed when the full length CPP32 was used. Therefore if CPP32 is cleaved at Asp28, CPP32 appears to be made up of two subunits of relative molecular masses of 17 kDa and 11 kDa. However, the exact Asp cleavage sites that are utilized to generate active CPP32 remains to be determined by amino acid sequencing. The GST-Mch2α preparation contains two major bands that migrate as ~31–32 kDa and ~34–35 kDa proteins. This is consistent with cleavage at Asp23, Asp32 or Asp40 of Mch2α. These GST-Mch2α cleavage products are larger than the GST-CPP32 product because of the presence of extra 33 amino acids in the GST-Mch2α fusion construct that are derived from the 5' untranslated region of Mch2α. A minor band of ~27 kDa is also present in this preparation that could be due to cleavage at a site near the C-terminus of the GST peptide itself. The majority of GST-Mch2β was expressed in *E. coli* in occlusion bodies and was not cleaved.

Analysis of the Enzymatic Activities of Mch2, CPP32 and ICE Using Fluorogenic Tetrapeptides After establishing that Mch2 and CPP32 can autoprocess in bacteria, their enzymatic activity were tested using two fluorogenic peptide substrates, YVAD-AMC (SEQ ID NO:8) and DEVD-AMC (SEQ ID NO:3). The YVAD (SEQ ID NO:8) pentapeptide is the ICE cleavage site in pro-IL1β and the DEVD (SEQ ID NO:9) tetrapeptide is a site present in PARP that is cleaved by an ICE-like protein during apoptosis. The enzymatic activities of Mch2α, Mch2β, CPP32 and ICEγ, in total bacterial extracts from cells expressing these enzymes as GST-fusion proteins was studied using the YVAD-AMC (SEQ ID NO:8) and DEVD-AMC (SEQ ID NO:3) tetrapeptides as substrates. Both ICEγ and CPP32 were able to cleave the YVAD (SEQ ID NO:10) substrate, although ICEγ was about 3-fold more active than CPP32 in cleaving this substrate. No detectable enzymatic activity was observed with Mch2α or Mch2β towards this substrate. On the other hand, Mch2α (but not Mch2β), ICEγ and CPP32 were able to cleave the DEVD substrate (SEQ ID NO:9). CPP32 is much more active towards this substrate than ICEγ or Mch2α. Assuming that the bacterial extracts contain similar amount of each enzyme, CPE32 was found to be ~150 fold more active than ICEγ or Mch2α in cleaving the DEVD substrate (SEQ ID NO:9) as determined from the initial rate of the reactions. The purified GST-fusion products or the GST control extract had no enzymatic activity with either of the substrates.

Mch2 and CPP32 Can Cleave PARP

In apoptotic cells, nuclear proteins such as PARP, lamins and the 70-kDa protein component of the Ul small nuclear ribonucleoprotein are cleaved specifically by an unknown ICE-like cysteine protease(s). Cleavage of human PARP at the DEVD (SEQ ID NO:9) site (amino acid 211–214) would generate a large protein product of predicted molecular mass of 89.3 kDa (amino acids 215–1014). Western blot analysis of human PARP after incubation with recombinant Mch2α, Mch2β, ICEγ or CPP32 was performed using the 4C10-5 antibody. This antibody recognizes an epitope in the 41 kDa C-terminal chymotryptic fragment of PARP. CPP32 cleaved PARP to generate a major band of ~90 kDa and a minor band of 57 kDa. The 90 kDa band was most probably generated by cleaving the DEVD (SEQ ID NO:9) site at residue 214 of PARP. This cleavage product is believed to correspond to an 85 kDa PARP cleavage product which has been described in apoptotic cells. The 57 kDa cleavage product is probably generated by cleavage at a site C-terminal to the DEVD (SEQ ID NO:9) site. This product was not detected with the C-2-10 antibody used in a previous study. This is probably because it recognizes an epitope that is N-terminal to the epitope that is recognized by the 4C10-5 antibody used in the present study. Mch2α also cleaved PARP to generate a major product of ~83 kDa and a minor product of ~57 kDa similar to that obtained with CPP32. PARP was not cleaved by Mch2β or ICEγ. These data suggest that both CPP32 and Mch2α can cleave PARP The major cleavage product obtained with Mch2α is smaller in size than the one obtained with CPP32, suggesting that the Mch2α cleavage site is C-terminal to the CPP32 cleavage site. Furthermore, the deletion in Mch2β abrogates its enzymatic activity.

Expression of Mch2α in Sf9 Cells Induces Apoptosis

To test whether expression of Mch2α has a similar apoptotic effect, Sf9 cells were infected with a recombinant baculovirus expressing Mch2α or Mch2β under the polyhedron promoter. Cells were also infected with the wild type virus and the recombinant ICE baculovirus as controls. Morphological, biochemical and viability analyses revealed that cells infected with ICE or Mch2α, but not with the wild type virus or Mch2β, had several characteristic signs of apoptosis including cytoplasmic membrane blebbing, nuclear fragmentation and condensation, and internucleosomal DNA cleavage. A decrease in viability similar to that observed previously with cells expressing ICE or CPP32 was also observed in cells expressing Mch2α, but not Mch2β.

The novel apoptotic cysteine protease named Mch2 was cloned using a PCR approach designed to identify and clone novel members of the Ced3/ICE-like apoptotic cysteine protease family. The amino acid sequence and predicted structure of Mch2 is similar to that of ICE and the other members of this family such as CED-3, CPP32 and Ich-1. Mch2α and CPP32 require an Asp residue in the P1 position of the peptide substrate DEVD-AMC (SEQ ID NO:3), suggesting that they have a similar substrate requirement as ICE.

The data show clearly that PARP is a substrate for both Mch2α and CPP32. Similar to ICE and Ich-1, the activity of Mch2 might be regulated by alternative splicing. An alternatively spliced isoform, Mch2β, was also isolated. Like Ich-1s, Mch2β could be a dominant inhibitor of Mch2α and could function as a negative regulator of apoptosis. Alternatively, if this form is cleaved to generate a functional p11 subunit, it may then serve as an activator of Mch2.

Consequently, the alternatively spliced isoforms of these enzymes may play a critical role in their activation or inhibition. Tissue specific regulation of the level of expression of these isoforms might be responsible for sensitivity or resistance to induction of apoptosis. The isolation and characterization of novel members of this important class of cysteine proteases will enhance the efforts to identify their endogenous substrates and regulators and to design specific drugs that will regulate their activity.

We claim:

1. A method of identifying inhibitors of Mch2α activity comprising the steps of:

performing a test assay by contacting an Mch2α with a substrate in the presence of a test compound under conditions in which said Mch2α processes said substrate in the absence of said test compound, determining whether said substrate is processed.

2. A method of identifying activators of Mch2α activity comprising the steps of:

performing a test assay by contacting an Mch2α with a substrate in the presence of a test compound under conditions in which said Mch2α processes said substrate in the absence of said test compound, comparing the rate of processing of the substrate in the presence of the test compound to the rate of processing the substrate in the absence of the compound.

* * * * *

SEQUENCE LISTING

```
(1) GENERAL INFORMATION:

   (iii) NUMBER OF SEQUENCES: 10


(2) INFORMATION FOR SEQ ID NO:1:

     (i) SEQUENCE CHARACTERISTICS:
          (A) LENGTH: 5 amino acids
          (B) TYPE: amino acid
          (D) TOPOLOGY: linear

    (ii) MOLECULE TYPE: protein

    (xi) SEQUENCE DESCRIPTION: SEQ ID NO:1:

Gln Ala Cys Arg Gly
1               5


(2) INFORMATION FOR SEQ ID NO:2:

     (i) SEQUENCE CHARACTERISTICS:
          (A) LENGTH: 5 amino acids
          (B) TYPE: amino acid
```

```
          (D) TOPOLOGY: linear

    (ii) MOLECULE TYPE: protein

    (xi) SEQUENCE DESCRIPTION: SEQ ID NO:2:

Gly Ser Trp Phe Ile
1               5


(2) INFORMATION FOR SEQ ID NO:3:

     (i) SEQUENCE CHARACTERISTICS:
          (A) LENGTH: 7 amino acids
          (B) TYPE: amino acid
          (D) TOPOLOGY: linear

    (ii) MOLECULE TYPE: protein

    (xi) SEQUENCE DESCRIPTION: SEQ ID NO:3:

Asp Glu Val Asp Ala Met Cys
1               5


(2) INFORMATION FOR SEQ ID NO:4:

     (i) SEQUENCE CHARACTERISTICS:
          (A) LENGTH: 1545 base pairs
          (B) TYPE: nucleic acid
          (C) STRANDEDNESS: double
          (D) TOPOLOGY: unknown

    (ii) MOLECULE TYPE: cDNA

    (ix) FEATURE:
          (A) NAME/KEY: CDS
          (B) LOCATION: 79..957

    (xi) SEQUENCE DESCRIPTION: SEQ ID NO:4:

CCGAGGGCGG GGCCGGGCCC GGGAGCCTGT GGCTTCAGGA AGAGGAGGGC AAGGTGTCTG      60

GCTGCGCGTT TGGCTGCA ATG AGC TCG GCC TCG GGG CTC CGC AGG GGG CAC       111
                    Met Ser Ser Ala Ser Gly Leu Arg Arg Gly His
                      1               5                  10

CCG GCA GGT GGG GAA GAA AAC ATG ACA GAA ACA GAT GCC TTC TAT AAA       159
Pro Ala Gly Gly Glu Glu Asn Met Thr Glu Thr Asp Ala Phe Tyr Lys
             15                  20                  25

AGA GAA ATG TTT GAT CCG GCA GAA AAG TAC AAA ATG GAC CAC AGG AGG       207
Arg Glu Met Phe Asp Pro Ala Glu Lys Tyr Lys Met Asp His Arg Arg
        30                  35                  40

AGA GGA ATT GCT TTA ATC TTC AAT CAT GAG AGG TTC TTT TGG CAC TTA       255
Arg Gly Ile Ala Leu Ile Phe Asn His Glu Arg Phe Phe Trp His Leu
    45                  50                  55

ACA CTG CCA GAA AGG CGG CGC ACC TGC GCA GAT AGA GAC AAT CTT ACC       303
Thr Leu Pro Glu Arg Arg Arg Thr Cys Ala Asp Arg Asp Asn Leu Thr
 60                  65                  70                  75

CGC AGG TTT TCA GAT CTA GGA TTT GAA GTG AAA TGC TTT AAT GAT CTT       351
Arg Arg Phe Ser Asp Leu Gly Phe Glu Val Lys Cys Phe Asn Asp Leu
                 80                  85                  90

AAA GCA GAA GAA CTA CTG CTC AAA ATT CAT GAG GTG TCA ACT GTT AGC       399
Lys Ala Glu Glu Leu Leu Leu Lys Ile His Glu Val Ser Thr Val Ser
             95                 100                 105

CAC GCA GAT GCC GAT TGC TTT GTG TGT GTC TTC CTG AGC CAT GGC GAA       447
His Ala Asp Ala Asp Cys Phe Val Cys Val Phe Leu Ser His Gly Glu
        110                 115                 120

GGC AAT CAC ATT TAT GCA TAT GAT GCT AAA ATC GAA ATT CAG ACA TTA       495
Gly Asn His Ile Tyr Ala Tyr Asp Ala Lys Ile Glu Ile Gln Thr Leu
    125                 130                 135

ACT GGC TTG TTC AAA GGA GAC AAG TGT CAC AGC CTG GTT GGA AAA CCC       543
```

```
Thr Gly Leu Phe Lys Gly Asp Lys Cys His Ser Leu Val Gly Lys Pro
140                 145                 150                 155

AAG ATA TTT ATC ATC CAG GCA TGT CGG GGA AAC CAG CAC GAT GTG CCA      591
Lys Ile Phe Ile Ile Gln Ala Cys Arg Gly Asn Gln His Asp Val Pro
                160                 165                 170

GTC ATT CCT TTG GAT GTA GTA GAT AAT CAG ACA GAG AAG TTG GAC ACC      639
Val Ile Pro Leu Asp Val Val Asp Asn Gln Thr Glu Lys Leu Asp Thr
            175                 180                 185

AAC ATA ACT GAG GTG GAT GCA GCC TCC GTT TAC ACG CTG CCT GCT GGA      687
Asn Ile Thr Glu Val Asp Ala Ala Ser Val Tyr Thr Leu Pro Ala Gly
        190                 195                 200

GCT GAC TTC CTC ATG TGT TAC TCT GTT GCA GAA GGA TAT TAT TCT CAC      735
Ala Asp Phe Leu Met Cys Tyr Ser Val Ala Glu Gly Tyr Tyr Ser His
    205                 210                 215

CGG GAA ACT GTG AAC GGC TCA TGG TAC ATT CAA GAT TTG TGT GAG ATG      783
Arg Glu Thr Val Asn Gly Ser Trp Tyr Ile Gln Asp Leu Cys Glu Met
220                 225                 230                 235

TTG GGA AAA TAT GGC TCC TCC TTA GAG TTC ACA GAA CTC CTC ACA CTG      831
Leu Gly Lys Tyr Gly Ser Ser Leu Glu Phe Thr Glu Leu Leu Thr Leu
                240                 245                 250

GTG AAC AGG AAA GTT TCT CAG CGC CGA GTG GAC TTT TGC AAA GAC CCA      879
Val Asn Arg Lys Val Ser Gln Arg Arg Val Asp Phe Cys Lys Asp Pro
            255                 260                 265

AGT GCA ATT GGA AAG AAG CAG GTT CCC TGT TTT GCC TCA ATG CTA ACT      927
Ser Ala Ile Gly Lys Lys Gln Val Pro Cys Phe Ala Ser Met Leu Thr
        270                 275                 280

AAA AAG CTG CAT TTC TTT CCA AAA TCT AAT TAATTAATAG AGGCTATCTA        977
Lys Lys Leu His Phe Phe Pro Lys Ser Asn
    285                 290

ATTTCACACT CTGTATTGAA AATGGCTTTC TCAGCCAGGC GTGGTTACTC ACACCTGTAA   1037

TCCCAGCACT TTGGGAGTCC AAGGTGGGCG GATCACCTGA GGTCGGGAGT TCGAGACCAG   1097

CCTGACCAAC ATGGCAGAAG CCCCGCCTCT ACTAAAAATG CAAAAAAAAA TTTAGCTAGG   1157

CATGGCGGCG CATGCCTGCA ATCCCAGCTA CTTGGAAGGC TGAGGCAGGA GAATCACTTG   1217

AACCCAGGAG GTGGAGGCTG CGGTGAGCCG AGCATTGCGC CATTGCACTC CAGCCTGGGC   1277

AACGAGTGAA ACTCCGTCTC AAAAAAAAAG AAAATGTCTT TCTCTTCCTT TTATATAAAT   1337

ATCGTTAGGG TGAAGCATTA TGGTCTAATG ATTCAAATGT TTTAAAGTTT AATGCCTAGC   1397

AGAGAACTGC CTTAAAAAAA AAAAGTTCAT GTTGGCCATG GTGAAAGGGT TTGATATGGA   1457

GAAACAAAAT CCTCAGGAAA TTAGATAAAT AAAAATTTAT AAGCATTTGT ATTATTTTTT   1517

AATAAACTGC AGGGTTACAC AAAAATCT                                      1545
```

(2) INFORMATION FOR SEQ ID NO:5:

(i) SEQUENCE CHARACTERISTICS:
(A) LENGTH: 293 amino acids
(B) TYPE: amino acid
(D) TOPOLOGY: linear (ii) MOLECULE TYPE: protein (xi) SEQUENCE DESCRIPTION: SEQ ID NO:5:

```
Met Ser Ser Ala Ser Gly Leu Arg Arg Gly His Pro Ala Gly Gly Glu
  1               5                  10                  15

Glu Asn Met Thr Glu Thr Asp Ala Phe Tyr Lys Arg Glu Met Phe Asp
             20                  25                  30

Pro Ala Glu Lys Tyr Lys Met Asp His Arg Arg Arg Gly Ile Ala Leu
         35                  40                  45
```

```
Ile Phe Asn His Glu Arg Phe Phe Trp His Leu Thr Leu Pro Glu Arg
     50                  55                  60

Arg Arg Thr Cys Ala Asp Arg Asp Asn Leu Thr Arg Arg Phe Ser Asp
 65                  70                  75                  80

Leu Gly Phe Glu Val Lys Cys Phe Asn Asp Leu Lys Ala Glu Glu Leu
                 85                  90                  95

Leu Leu Lys Ile His Glu Val Ser Thr Val Ser His Ala Asp Ala Asp
            100                 105                 110

Cys Phe Val Cys Val Phe Leu Ser His Gly Glu Gly Asn His Ile Tyr
        115                 120                 125

Ala Tyr Asp Ala Lys Ile Glu Ile Gln Thr Leu Thr Gly Leu Phe Lys
    130                 135                 140

Gly Asp Lys Cys His Ser Leu Val Gly Lys Pro Lys Ile Phe Ile Ile
145                 150                 155                 160

Gln Ala Cys Arg Gly Asn Gln His Asp Val Pro Val Ile Pro Leu Asp
                165                 170                 175

Val Val Asp Asn Gln Thr Glu Lys Leu Asp Thr Asn Ile Thr Glu Val
            180                 185                 190

Asp Ala Ala Ser Val Tyr Thr Leu Pro Ala Gly Ala Asp Phe Leu Met
        195                 200                 205

Cys Tyr Ser Val Ala Glu Gly Tyr Tyr Ser His Arg Glu Thr Val Asn
    210                 215                 220

Gly Ser Trp Tyr Ile Gln Asp Leu Cys Glu Met Leu Gly Lys Tyr Gly
225                 230                 235                 240

Ser Ser Leu Glu Phe Thr Glu Leu Leu Thr Leu Val Asn Arg Lys Val
                245                 250                 255

Ser Gln Arg Arg Val Asp Phe Cys Lys Asp Pro Ser Ala Ile Gly Lys
            260                 265                 270

Lys Gln Val Pro Cys Phe Ala Ser Met Leu Thr Lys Lys Leu His Phe
        275                 280                 285

Phe Pro Lys Ser Asn
    290
```

(2) INFORMATION FOR SEQ ID NO:6:

(i) SEQUENCE CHARACTERISTICS:
(A) LENGTH: 1313 base pairs
(B) TYPE: nucleic acid
(C) STRANDEDNESS: double
(D) TOPOLOGY: unknown (ii) MOLECULE TYPE: cDNA (ix) FEATURE:
(A) NAME/KEY: CDS
(B) LOCATION: 1..612

(xi) SEQUENCE DESCRIPTION: SEQ ID NO:6:

```
ATG AGC TCG GCC TCG GGG CTC CGC AGG GGG CAC CCG GCA GTG TCA ACT       48
Met Ser Ser Ala Ser Gly Leu Arg Arg Gly His Pro Ala Val Ser Thr
  1               5                  10                  15

GTT AGC CAC GCA GAT GCC GAT TGC TTT GTG TGT GTC TTC CTG AGC CAT       96
Val Ser His Ala Asp Ala Asp Cys Phe Val Cys Val Phe Leu Ser His
             20                  25                  30

GGC GAA GGC AAT CAC ATT TAT GCA TAT GAT GCT AAA ATC GAA ATT CAG      144
Gly Glu Gly Asn His Ile Tyr Ala Tyr Asp Ala Lys Ile Glu Ile Gln
        35                  40                  45

ACA TTA ACT GGC TTG TTC AAA GGA GAC AAG TGT CAC AGC CTG GTT GGA      192
Thr Leu Thr Gly Leu Phe Lys Gly Asp Lys Cys His Ser Leu Val Gly
     50                  55                  60
```

```
AAA CCC AAG ATA TTT ATC ATC CAG GCA TGT CGG GGA AAC CAG CAC GAT      240
Lys Pro Lys Ile Phe Ile Ile Gln Ala Cys Arg Gly Asn Gln His Asp
 65                  70                  75                  80

GTG CCA GTC ATT CCT TTG GAT GTA GTA GAT AAT CAG ACA GAG AAG TTG      288
Val Pro Val Ile Pro Leu Asp Val Val Asp Asn Gln Thr Glu Lys Leu
                 85                  90                  95

GAC ACC AAC ATA ACT GAG GTG GAT GCA GCC TCC GTT TAC ACG CTG CCT      336
Asp Thr Asn Ile Thr Glu Val Asp Ala Ala Ser Val Tyr Thr Leu Pro
            100                 105                 110

GCT GGA GCT GAC TTC CTC ATG TGT TAC TCT GTT GCA GAA GGA TAT TAT      384
Ala Gly Ala Asp Phe Leu Met Cys Tyr Ser Val Ala Glu Gly Tyr Tyr
        115                 120                 125

TCT CAC CGG GAA ACT GTG AAC GGC TCA TGG TAC ATT CAA GAT TTG TGT      432
Ser His Arg Glu Thr Val Asn Gly Ser Trp Tyr Ile Gln Asp Leu Cys
    130                 135                 140

GAG ATG TTG GGA AAA TAT GGC TCC TCC TTA GAG TTC ACA GAA CTC CTC      480
Glu Met Leu Gly Lys Tyr Gly Ser Ser Leu Glu Phe Thr Glu Leu Leu
145                 150                 155                 160

ACA CTG GTG AAC AGG AAA GTT TCT CAG CGC CGA GTG GAC TTT TGC AAA      528
Thr Leu Val Asn Arg Lys Val Ser Gln Arg Arg Val Asp Phe Cys Lys
                165                 170                 175

GAC CCA AGT GCA ATT GGA AAG AAG CAG GTT CCC TGT TTT GCC TCA ATG      576
Asp Pro Ser Ala Ile Gly Lys Lys Gln Val Pro Cys Phe Ala Ser Met
            180                 185                 190

CTA ACT AAA AAG CTG CAT TTC TTT CCA AAA TCT AAT TAATTAATAG           622
Leu Thr Lys Lys Leu His Phe Phe Pro Lys Ser Asn
        195                 200

AGGCTATCTA ATTTCACACT CTGTATTGAA AATGGCTTTC TCAGCCAGGC GTGGTTACTC    682

ACACCTGTAA TCCCAGCACT TTGGGAGTCC AAGGTGGGCG GATCACCTGA GGTCGGGAGT    742

TCGAGACCAG CCTGACCAAC ATGGCAGAAG CCCCGCCTCT ACTAAAAATG CAAAAAAAAA    802

TTTAGCTAGG CATGGCGGCG CATGCCTGCA ATCCCAGCTA CTTGGAAGGC TGAGGCAGGA    862

GAATCACTTG AACCCAGGAG GTGGAGGCTG CGGTGAGCCG AGCATTGCGC CATTGCACTC    922

CAGCCTGGGC AACGAGTGAA ACTCCGTCTC AAAAAAAAAG AAAATGTCTT TCTCTTCCTT    982

TTATATAAAT ATCGTTAGGG TGAAGCATTA TGGTCTAATG ATTCAAATGT TTTAAAGTTT   1042

AATGCCTAGC AGAGAACTGC CTTAAAAAAA AAAAGTTCAT GTTGGCCATG GTGAAAGGGT   1102

TTGATATGGA GAAACAAAAT CCTCAGGAAA TTAGATAAAT AGAAATTTAT AAGCATTTGT   1162

ATTATTTTTT AATAAACTGC AGGGTTACAC CAAAATCTAG CTGATTTAAC TTGTATTTTG   1222

TCACTTTTTT ATAAAAGTTT ATTGTTTGAT GTTTTTAAAG GTTTTTGAAA TCCAGGAATT   1282

AAATCATCCC TTAATAAAAT ATTCGAAATT C                                  1313
```

(2) INFORMATION FOR SEQ ID NO:7:

(i) SEQUENCE CHARACTERISTICS:
(A) LENGTH: 204 amino acids
(B) TYPE: amino acid
(D) TOPOLOGY: linear (ii) MOLECULE TYPE: protein (xi) SEQUENCE DESCRIPTION: SEQ ID NO:7:

```
Met Ser Ser Ala Ser Gly Leu Arg Arg Gly His Pro Ala Val Ser Thr
  1               5                  10                  15

Val Ser His Ala Asp Ala Asp Cys Phe Val Cys Val Phe Leu Ser His
             20                  25                  30

Gly Glu Gly Asn His Ile Tyr Ala Tyr Asp Ala Lys Ile Glu Ile Gln
```

-continued

```
        35                  40                  45

Thr Leu Thr Gly Leu Phe Lys Gly Asp Lys Cys His Ser Leu Val Gly
     50                  55                  60

Lys Pro Lys Ile Phe Ile Ile Gln Ala Cys Arg Gly Asn Gln His Asp
 65                  70                  75                  80

Val Pro Val Ile Pro Leu Asp Val Val Asp Asn Gln Thr Glu Lys Leu
                 85                  90                  95

Asp Thr Asn Ile Thr Glu Val Asp Ala Ala Ser Val Tyr Thr Leu Pro
            100                 105                 110

Ala Gly Ala Asp Phe Leu Met Cys Tyr Ser Val Ala Glu Gly Tyr Tyr
        115                 120                 125

Ser His Arg Glu Thr Val Asn Gly Ser Trp Tyr Ile Gln Asp Leu Cys
    130                 135                 140

Glu Met Leu Gly Lys Tyr Gly Ser Ser Leu Glu Phe Thr Glu Leu Leu
145                 150                 155                 160

Thr Leu Val Asn Arg Lys Val Ser Gln Arg Arg Val Asp Phe Cys Lys
                165                 170                 175

Asp Pro Ser Ala Ile Gly Lys Lys Gln Val Pro Cys Phe Ala Ser Met
            180                 185                 190

Leu Thr Lys Lys Leu His Phe Phe Pro Lys Ser Asn
        195                 200


(2) INFORMATION FOR SEQ ID NO:8:

     (i) SEQUENCE CHARACTERISTICS:
          (A) LENGTH: 7 amino acids
          (B) TYPE: amino acid
          (D) TOPOLOGY: linear

    (ii) MOLECULE TYPE: protein

    (xi) SEQUENCE DESCRIPTION: SEQ ID NO:8:

Tyr Val Ala Asp Ala Met Cys
1               5


(2) INFORMATION FOR SEQ ID NO:9:

     (i) SEQUENCE CHARACTERISTICS:
          (A) LENGTH: 4 amino acids
          (B) TYPE: amino acid
          (D) TOPOLOGY: linear

    (ii) MOLECULE TYPE: protein

    (xi) SEQUENCE DESCRIPTION: SEQ ID NO:9:

Asp Glu Val Asp
1


(2) INFORMATION FOR SEQ ID NO:10:

     (i) SEQUENCE CHARACTERISTICS:
          (A) LENGTH: 4 amino acids
          (B) TYPE: amino acid
          (D) TOPOLOGY: linear

    (ii) MOLECULE TYPE: protein

    (xi) SEQUENCE DESCRIPTION: SEQ ID NO:10:

Tyr Val Ala Asp
```